Aug. 20, 1968 D. L. ARMSTRONG ETAL Plant Pat. 2,829
ROSE PLANT
Filed Feb. 8, 1967
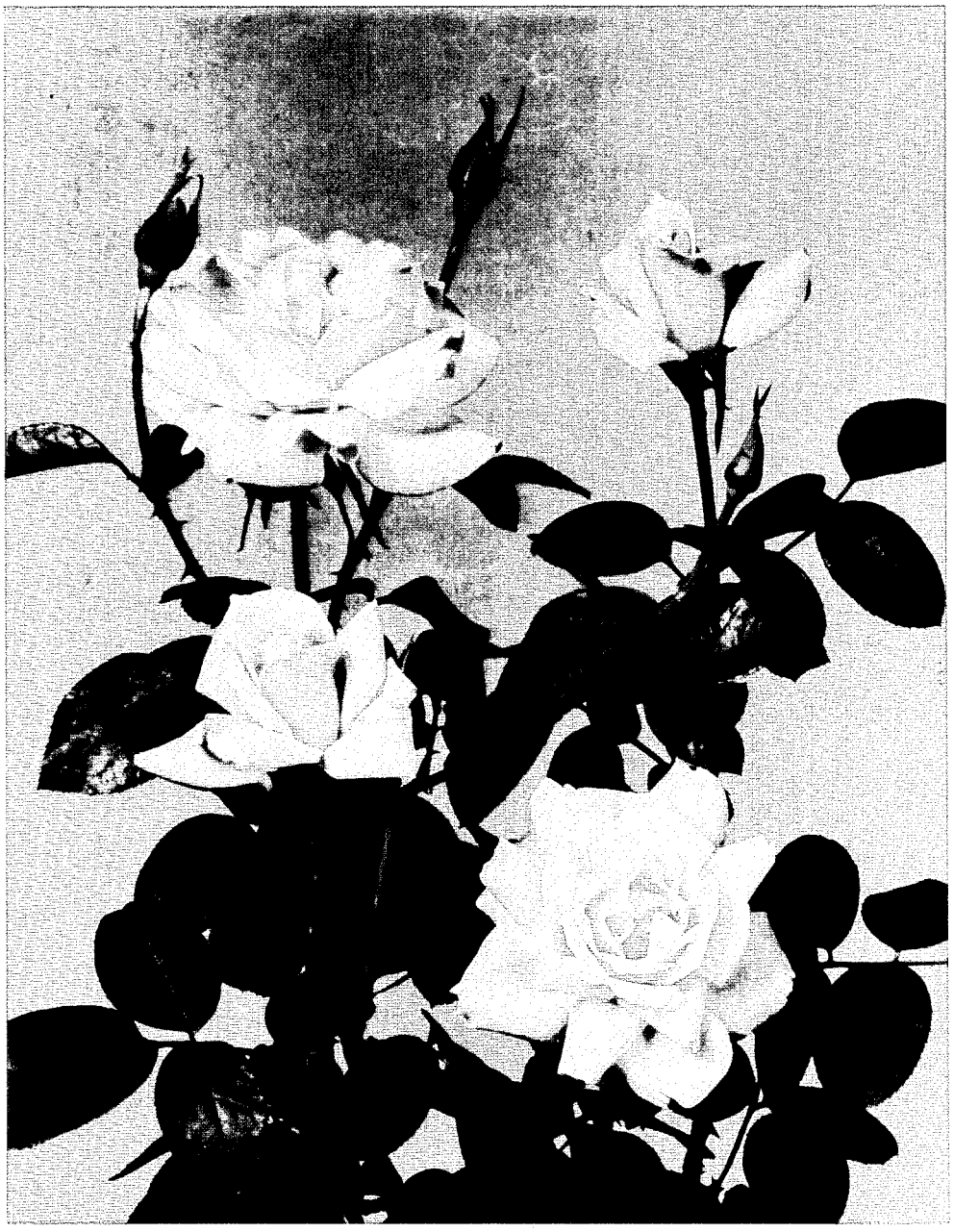
Inventors.
D. L. Armstrong
H. C. Swim
By: Robb & Robb
Attorneys.

United States Patent Office

Plant Pat. 2,829
Patented Aug. 20, 1968

2,829
ROSE PLANT

David L. Armstrong and Herbert C. Swim, Ontario, Calif., assignors to Armstrong Nurseries, Inc., Ontario, Calif., a corporation of California Filed Feb. 8, 1967, Ser. No. 614,756
1 Claim. (Cl. Pit.—18)

The present invention relates to a new and distinct variety of rose plant of the grandiflora class, which was originated by us by crossing the variety known as "Charlotte Armstrong" (Plant Patent No. 455) with the variety known as "Cherry Glow" (Plant Patent No. 1,490), the former being the seed parent and the latter being the pollen parent.

The primary objective of this breeding was to produce a new and improved rose variety having the vigor and floriferousness of the parent variety "Cherry Glow," combined with the excellent urn-shaped bud form of both parents, the large flower size and flower form of the parent variety "Charlotte Armstrong," and with the flower color being in the red to pink color range. This objective was fully achieved, along with other desirable features, as evidenced by the following unique combination of characteristics which are outstanding in the new variety and which distinguish it from its parents, as well as from all other varieties of which we are aware:

(1) A vigorous and attractive plant habit, intermediate upright and spreading;

(2) Medium to large, dark green, leathery, semi-glossy and disease resistant foliage;

(3) A very floriferous habit, with the flowers borne on medium length stems and borne both singly and in small clusters typical of the grandiflora class;

(4) Attractive urn-shaped flower buds, and a relatively high-centered open flower form, and showing petals reflexed in a manner similar to those of "Charlotte Armstrong";

(5) A flower size from medium to large, with from 25 to 35 petals; and (6) A distinctive and attractive flower color ranging between Neyron Rose and Dawn Pink, with darker pink on the reverse side of the petals.

In comparison with its seed parent "Charlotte Armstrong," the new variety primarily differs therefrom by being a bicolor, with light pink on one side and darker pink on the reverse side of the flower petals, as distinguished from the dark cerise pink or light red color of the flowers of "Charlotte Armstrong," and the plant of the new variety is more vigorous, with the leaves being more glossy than those of this parent.

As compared with its pollen parent "Cherry Glow," the new variety primarily differs therefrom by being a light and darker pink bicolor as aforementioned, whereas the flowers of "Cherry Glow" are red.

While the new variety resembles a fairly similar variety known as "Columbus Queen" (Plant Patent No. 2,170), it differs therefrom by having a more spreading plant habit, a somewhat greater tendency to bear flowers in small clusters, a slightly more bluish pink flower color, and an open flower form that is more high-centered, with the petals more definitely reflexed outward as typical of "Charlotte Armstrong."

Asexual reproduction of our new variety by budding, as performed at Ontario, Calif., shows that the foregoing characteristics and distinctions come true to form and are established and transmitted through succeeding propagations.

The accompanying drawing shows typical specimens of the vegetative growth and flowers of our new variety in different stages of development, with some of the flowers and vegetative growth being depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W) and Robert Ridgway's Color Standards and Nomenclature (hereinafter abbreviated as (R)), as indicated:

Type: Tall; bush; outdoor; seedling; for cut flowers and for garden decoration.
Class: Grandiflora.
Breeding: Seedling.
*Seed parent.*—"Charlotte Armstrong."
*Pollen parent.*—"Cherry Glow."
Propagation: Holds its distinguishing characteristics through succeeding propagations by budding.

*Flower*

Locality where grown and observed: Ontario, Calif.
Flowers borne: Sometimes singly, and sometimes two or three or more to stem; in irregular clusters; on strong stems of medium length.
Quantity of bloom: Abundant, outdoors.
Continuity: Nearly continuous during growing season.
Fragrance: Slight.
Bud:
*Peduncle.*—From average length to long; average caliper; erect; usually smooth, with several to many stipitate glands and few to several small prickles. Color—near Absinthe Green, Plate XXXI (R) overlaid with near Buffy Olive, Plate XXX (R) on side exposed to sun.
*Before calyx breaks.*—Size—medium. Form—medium length; pointed and ovoid.
*As calyx breaks.*—Color—between China Rose, Plate 024, page 111 (W) and Chrysanthemum Crimson, Plate 824/2, page 169 (W).
*Sepals.*—Usually with foliaceous appendages extending from ¼ to ½ of sepal length. Inner surface—with fine, wooly tomentum. Outer surface—usually with several to many small stipitate glands. Alternate margins—lined with fine wooly tomentum. Other margins—with several to many small stipitate glands and usually with small slender foliaceous parts.
*As first petal opens.*—Size—average. Form—from medium length to long, ovoid, and usually urn-shaped. Color: outside—near Phlox Pink, Plate 625 (W), page 77, blending with near Rose Bengal, Plate 25/1, page 25 (W) toward base of petal; inside—near Neyron Rose, Plate 623/2, page 76 (W), with small area at base of petal near attachment near Canary Yellow, Plate 2/1, page 2 (W).
*Opening.*—Opens up well; is not retarded or prevented from opening by cold, hot, wet or dry weather.
Bloom:
*Size (when fully open).*—From medium to large; from 4 inches to 5 inches.
*Petalage.*—Double; from 25 to 35 petals, plus 2 to 6 petaloids; arranged irregularly.
*Form.*—High-centered at first but becoming cupped to high-centered; petals being at first somewhat tightly cupped with tips reflexed outward, but becoming later at maturity more loosely flat to cupped, with tips reflexed outward; outside petals usually reflexed outward both along edges and apex of petal; intermediate petals usually reflexed outward along apex of petal; inside petals and petaloids usually arranged irregularly in center of flower.

Petals:

*Texture.*—Medium thickness; moderately leathery.

*Appearance.*—Inside—satiny. Outside—satiny.

*Shape.*—Outside—between round and broadly obovate, with apex flat and sometimes with 1 or 2 notches. Intermediate—obovate, with apex rounded to flat and sometimes with 1 or 2 notches. Inside—narrowly obovate, with apex rounded and sometimes with 1 or 2 notches.

This description of a newly opened flower was made from a rose grown outdoors during the month of August at Ontario, Calif.:

*Color.*—Outer petal: outside surface—between Rose Bengal, Plate 25/2, page 25 (W), and Solferino Purple, Plate 26/2, page 26 (W); inside surface—between Neyron Rose, Plate 623/3, page 76 (W), and Phlox Pink, Plate 625/3, page 77 (W); small area at base of petal near attachment near Canary Yellow, Plate 2/2, page 2 (W). Intermediate petal: outside surface—near Rhodamine Pink, Plate 527/2, page 138 (W); inside surface—near Dawn Pink, Plate 523/3, page 137 (W), with small area at base of petal near attachment near Canary Yellow, Plate 2/2, page 2 (W). Inner petal: outside surface—near Rhodamine Pink, Plate 527/2, page 138 (W); inside surface—near Dawn Pink, Plate 523/3, page 137 (W), with small area at base of petal near attachment near Sulphur Yellow, Plate 1/3, page 1 (W).

This description was made from a rose that was open for three days, outdoors during the month of August at Ontario, Calif.:

*Color.*—Outer petal: outside surface—between Tyrian Rose, Plate 24/2, page 24 (W), and Phlox Pink, Plate 625/1, page 77 (W); inside surface—near Dawn Pink, Plate 523/2, page 137 (W), with small area at base of petal near attachment near Sulphur Yellow, Plate 1/3, page 1 (W). Inner petal: outside surface—near Rhodamine Pink, Plate 527/2, page 138 (W); inside surface—near Dawn Pink, Plate 523/3, page 137 (W), with small area at base of petal near Sulphur Yellow, Plate 1/3, page 1 (W).

*General color effect.*—Newly opened flower—between Neyron Rose, Plate 623/2, page 76 (W), and Dawn Pink, Plate 523, page 137 (W). Three days open—between Neyron Rose, Plate 623/3, page 76 (W), and Dawn Pink, Plate 523/3, page 137 (W).

*Behavior.*—Drop off cleanly; not particularly affected by cold, hot, wet, dry weather.

*Flower longevity.*—On bush in garden—4 or 5 days in October. Cut roses grown outdoors kept at living-room temperatures—4 or 5 days in October.

*Reproductive organs*

Stamens: Average number; arranged regularly about pistils; a few mixed with petaloids.

Filaments: Medium length (from 6 mm. to 12 mm. long); most with anthers. Color—near Empire Yellow, Plate 603/1, page 66 (W).

Anthers: From small to medium size; all open approximately at once. Color:—upper side—margins near Indian Yellow, Plate 6/1, page 6 (W), with remainder near Lemon Yellow, Plate 4/2, page 4 (W); under side—margins near Indian Yellow, Plate 6/1, page 6 (W), with remainder near Lemon Yellow, Plate 4/2, page 4 (W).

Pollen: Moderate abundance. Color—near Saffron Yellow, Plate 7/1, page 7 (W).

Pistils: Average number (approximately 65).

Styles: Moderately even; from short to average length; thin caliper; bunched. Color—upper 1/2 of style near Straw Yellow, Plate 604/1, page 67 (W), with remainder near Primrose Yellow, Plate 601/2, page 65 (W).

Stigma: Color—near Straw Yellow, Plate 604/2, page 67 (W).

Ovaries: Usually all enclosed in calyx.

Hips: From short to average length; between globular and obovoid; thick; fleshy. Color (half mature)—near Lime Green, Plate XXXI (R).

Sepals: Fall soon; from medium length to long; straight. color: inside—near Lime Green, Plate XXXI (R); outside—near Rainette Green, Plate XXXI (R).

Seeds: Average number, from 15 to 35; from small to medium size.

*Plant*

Foliage:

*Leaves.*—Compound of usually 3 to 7 leaflets; abundant; from medium to large size; leathery; semi-glossy.

*Leaflets.*—Shape—broadly oval, but some leaflets nearly round, with apex acute. Base—round. Margin—simply serrate.

*Color.*—Mature: upper surface—near Forest Green, Plate XVII (R); under surface—near Biscay Green, Plate XVII (R). Young: upper surface—near Deep Dull Yellow-Green (2), Plate XXXII (R); under surface—near Absinthe Green, Plate XXXI (R).

*Rachis (the supporting stem of the compound leaf).*—From light to average size. Upper side—grooved; with few to several stipitate glands on edges. Under side—smooth; with several stipitate glands, and from none to few small prickles.

*Stipules.*—Medium length; from medium width to wide; with short points turning out at an angle of usually less than 45° toward the stem.

*Disease resistance.*—Better than average resistance to mildew, when compared with other varieties now in commerce grown under comparable conditions at Ontario, Calif.

Growth:

*Habit.*—Upright—spreading and much-branched.

*Growth.*—Vigorous.

*Canes.*—From medium caliper to heavy.

*Main stems.*—Color—near Citrine-Drab, Plate XL (R). Large prickles—several; medium length; hooked slightly downward; with from short to medium length narrow base; color—near Wood-Brown, Plate XL (R). Small prickles—from several to many; color—near Wood-Brown, Plate XL (R). Hairs—none.

*Branches.*—Color—near Rainette Green, Plate XXXI (R). Large prickles—from several to many; from short to medium length; hooked slightly downward; with from short to medium length narrow base; color—near Walnut Brown, Plate XXVIII (R). Small prickles—from several to many; color—near Walnut Brown, Plate XXVIII (R). Hairs—none.

*New shoots.*—Color—near Apple Green, Plate XVII (R), overlaid with near Buffy Olive, Plate XXX (R) on side exposed to the sun. Large prickles—several; medium length; hooked slightly downward; with from short to medium length narrow base; color—near Burnt Lake, Plate XII (R). Small prickles—from several to many; color—near Burnt Lake, Plate XII (R). Hairs—none.

We claim:

1. A new and distinct variety of rose plant of the grandiflora class, substantially as herein shown and described, characterized particularly as to novelty by the unique combination of a vigorous and attractive plant habit, intermediate upright and spreading, medium to large dark green, leathery, semi-glossy and disease resistant foliage, a very floriferous habit, with the flowers borne on medium length stems and borne both singly and in small clusters typical of the grandiflora class, attractive urn-shaped flower buds, and a relatively high-centered open flower form and showing petals reflexed in a manner similar to those of "Charlotte Armstrong," a flower size from medium to large, with from 25 to 35 petals, and a distinctive and attractive flower color ranging between Neyron Rose and Dawn Pink, with darker pink on the reverse side of the petals.

No references cited.

ROBERT E. BAGWILL, *Primary Examiner.*